United States Patent [19]

Dixon

[11] 4,094,923
[45] June 13, 1978

[54] ALKYLATION PROCESS UTILIZING DECREASING AMOUNTS OF OLEFIN IN RISER-REACTOR

[75] Inventor: Rolland E. Dixon, Bartlesville, Okla.

[73] Assignee: Phillips Petroleum Company, Bartlesville, Okla.

[21] Appl. No.: 765,328

[22] Filed: Feb. 3, 1977

[51] Int. Cl.² .............................................. C07C 3/54
[52] U.S. Cl. .............................................. 260/683.48
[58] Field of Search ...................... 260/683.48, 683.49, 260/683.51, 683.43

[56] References Cited

U.S. PATENT DOCUMENTS

| 2,399,353 | 4/1946 | Jones | 260/683.51 |
| 2,437,544 | 3/1948 | Marisic | 260/683.51 |
| 2,775,636 | 12/1956 | Rupp | 260/683.48 |
| 3,169,153 | 2/1965 | Walker et al. | 260/683.48 |
| 3,281,213 | 10/1966 | Waddill | 260/683.48 |
| 3,716,343 | 2/1973 | Chapman | 260/683.48 |
| 3,778,489 | 12/1973 | Parker et al. | 260/683.43 |

Primary Examiner—George Crasanakis

[57] ABSTRACT

High quality alkylate is produced by HF alkylation of isoparaffins with olefin in a riser-reactor-type cyclic alkylation process by charging the total isoparaffin feed and HF acid catalyst to the inlet of the riser-reactor and introducing separate spaced streams of olefin in decreasing quantities along the length of the riser-reactor under conditions such as to effect high isoparaffin to olefin molar ratios along the flow path thereby avoiding the detrimental effects of unavoidable increases in reaction temperature along the reaction flow path.

4 Claims, 3 Drawing Figures

ALKYLATION PROCESS UTILIZING DECREASING AMOUNTS OF OLEFIN IN RISER-REACTOR

This invention relates to an improved process for the production of high quality alkylate. In accordance with another aspect, this invention relates to an improved method of feeding reactants to an HF alkylation comprising parallel olefin and series isoparaffin introduction of feed to maximize octane number by increasing the isoparaffin to olefin ratio along the flow path. In accordance with another aspect, this invention relates to the cyclic flow path HF alkylation operation wherein the total isoparaffin feed along with total HF acid catalyst is introduced into the inlet of a riser-reactor and the olefin is introduced at spaced points along the length of the reactor in decreasing amounts so as to maintain the desirably high isoparaffin to olefin ratio along the flow path. In accordance with a further aspect, this invention relates to HF alkylation of isobutane with butylenes in a riser-reactor-type HF alkylation zone by charging the total feed isobutane to the lower portion of the riser-reactor and charging separate streams in decreasing quantities of butylenes into the upwardly flowing mass at injection points spaced along the riser-reactor so as to produce alkylate product of more uniform octane numbers rather than a mixture of alkylates with widely varing octane numbers as per conventional alkylation processes.

It is known in the art to react alkylatable hydrocarbons with alkylating hydrocarbons in the presence of an HF acid catalyst to produce alkylate. Alkylation of isoparaffins such as isobutane with olefins such as butylenes and/or propylene and/or alkyl fluorides is extremely fast in the presence of HF acid catalyst, as is practiced in what is called the reactor-riser-type alkylation wherein reactants pass through a cyclic path including in series and in open communication a vertical extended reaction zone, a settling zone, a cooling zone, and return to the reaction zone. Experience has shown that the heat rise attendant to the reaction is predominantly in the area of dispersion of mixed olefins, indicating that for all intents and purposes the majority of the reactor contact time is of lesser importance since the reaction leg height is needed to provide a density difference in the two legs of the reactor, and, thereby, flow of acid is induced. The reaction products are highly influenced by the isoparaffin to olefin ratio at the point of reaction; the higher this ratio the better the quality or higher octane of alkylate. One of the problems encountered in this type of operation is the unavoidable increase in reaction temperature along the reaction zone which tends to have a detrimental effect on octane value. The present invention is directed to an improved process whereby the reactants are introduced into the riser-reactor in such a manner as to offset the detrimental effect of high temperature on octane value, thereby resulting in an improved alkylate product.

Accordingly, an object of this invention is to provide an improved process for alkylation.

Another object of this invention is to provide an improved process for alkylation wherein the octane number of the alkylate produced is increased.

A further object of this invention is to provide an improved reactant feed system for HF alkylation wherein an increase in octane number is realized.

Other objects and aspects, as well as the several advantages of this invention, will be apparent to those skilled in the art upon a reading of the specificiation, the drawing, and the appended claims.

Figure 1:
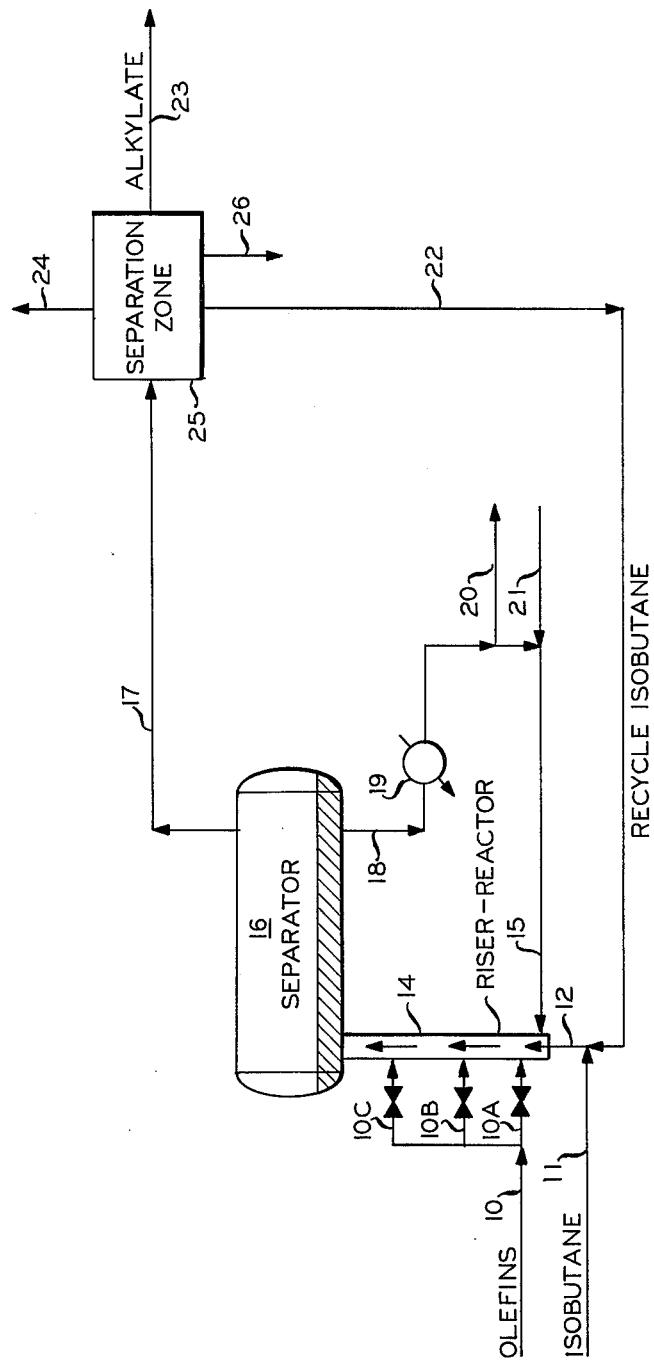
FIG. 1 represents an embodiment for the alkylation of isobutane.

In accordance with the invention, an improved process for production of high quality motor fuel alkylate is provided which comprises reacting an alkylatable hydrocarbon with an alkylating olefin in the presence of HF acid catalyst in a riser-reactor-type HF alkylation zone by charging the total isoparaffin feed and HF acid catalyst to the inlet of the reactor and introducing separate spaced streams of olefin in decreasing quantities along the length of the reaction zone without phase separation of hydrocarbon and HF catalyst within the riser-reactor.

In accordance with another embodiment to maximize octane number of alkylate produced by HF alkylation of isobutane with at least one olefin, e.g., propylene and/or butylenes, in a riser-reactor-type reaction system having a cyclic flow path, the isobutane to olefin mole ratio is maximized by charging the total feed isobutane along with total HF catalyst to a lower portion of the reactor-riser and charging separate streams in decreasing quantities of olefin feed into the upwardly flowing mass at injection points spaced along the riser-reactor to effect higher isobutane to olefin ratios along the flow path to account for detrimental effects of increasing temperature along the flow path.

The reaction conditions for carrying out the alkylation process of the present invention are well known in the art. The present invention is directed to an improved system of feeding isoparaffin, especially isobutane, and olefin, particularly propylene and/or butylenes, to a riser-reactor-type HF alkylation operation, thereby maximizing octane number by increasing the isobutane to olefin ratio along the flow path in such increments as to offset the detrimental effect of the increased temperature along the flow path on octane value. It has been found that the octane number of the alkylate formed along the reaction path is therefore kept constant which results in a product containing alkylates of more uniform octane numbers rather than an alkylate mixture with widely varying octane numbers, as is usually obtained in conventional alkylation processes.

The alkylation reaction is carried out with the hydrocarbon reactants in the liquid phase; however, the reactants need not be normally liquid hydrocarbons. The invention is particularly applicable to the alkylation of isobutane with an olefin mixture such as butylenes, but other olefins can also be used. The reaction conditions can vary in temperature from, say, about −40° F (−40° C) to as high as 150° F (66° C) and can be carried out under sufficient pressure to maintain liquid phase conditions. While generally applicable to the alkylation of hydrocarbons, the present invention is particularly effective for the alkylation of saturated branched chain paraffins such as isobutane and/or isopentane with propylene and/or butylenes in the presence of hydrofluoric acid. In the alkylation of isoparaffins with butylenes, the molar ratio of isoparaffin to olefin usually will range from 4:1 to about 20:1. It is presently preferred that the molar ratio of isoparaffin to olefin increase from the inlet end of the reaction zone to the outlet end of the reaction zone. The volume ratio of HF to total hydrocarbons will be in the range of 0.2:1 to about 20:1.

A better understanding of the invention will be obtained upon reference to the drawing which represents diagrammatically one embodiment of the invention for the alkylation of isobutane with isobutenes in a cyclic HF alkylation operation.

Referring now to the drawing, fresh or feed isobutane in line 11 and recycle isobutane in line 22 are combined in line 12 and introduced into a lower portion of riser-reactor 14 along with recycle HF catalyst introduced by way of line 15.

Olefin in line 10 is introduced in accordance with the invention at spaced points 10A, 10B, and 10C along the length of riser-reactor 14. The amount of olefin introduced into riser-reactor 14 decreases from line 10A to line 10C. Although three points of introduction are shown in the drawing, it should be realized that any desired number of points of introduction of olefin can be employed so long as sufficient olefin is introduced to maintain the high isobutane to olefin mole ratio in the reaction flow path in riser-reactor 14.

Within vertical riser-reactor 14 the hydrocarbon reactants and HF are maintained under alkylation conditions and passed upwardly through vertical reaction zone 14 under liquid phase conditions and introduced into the base of settling chamber 16.

Within settling chamber 16 the reaction mass removed from the alkylation zone 14 is allowed to separate into an upper hydrocarbon phase and a lower HF catalyst liquid phase. The hydrocarbon phase is removed from an upper portion of settling zone 16 by way of line 17 and passed to further processing in separation zone 25 wherein the hydrocarbons can be subjected to fractionation to recover desired fractions of product.

Within separation zone 25 which can involve a plurality of separation or fractionation zones, alkylate product of high octane value is removed by way of line 23 and the components lighter than isobutane are removed by way of line 24 for further processing, as desired. Isobutane recovered in separation zone 25 can be recycled by way of line 22 to riser-reactor 14 for reuse. Norman butane can be removed via 26. One of the advantages of the instant invention, i.e., parallel olefin and series isobutane feed to the reaction zone, is the reduced need of recycle isobutane to the alkylation zone. It has been found in some operations that only about one-half as much recycle isobutane is required according to the invention to attain the desired goal of octane values which allows control of the alkylation at preselected isobutane to olefin ratios to ultimately produce uniform high octane alkylate. One of the major costs in HF alkylation plants is the need for a deisobutanizing step to recover isobutane for recycle to the alkylation step. This cost can be substantially reduced in accordance with the present invention.

The HF catalyst level in settling zone 16 is maintained at a desirable level, usually a relatively low level, so that the hydrocarbon portion of the reaction mass is not detained in contact with the HF catalyst in the settler for a prolonged period. HF catalyst is continually removed from the base or lower portion of settling zone 16 by way of line 18 and passed through cooler 19 and then through line 15 for recontact with newly introduced isobutane by way of line 12. Catalyst can be withdrawn by way of line 20 for regeneration and new and/or regenerated catalyst can be reintroduced into the system by way of line 21.

SPECIFIC EXAMPLE

Figure 2:
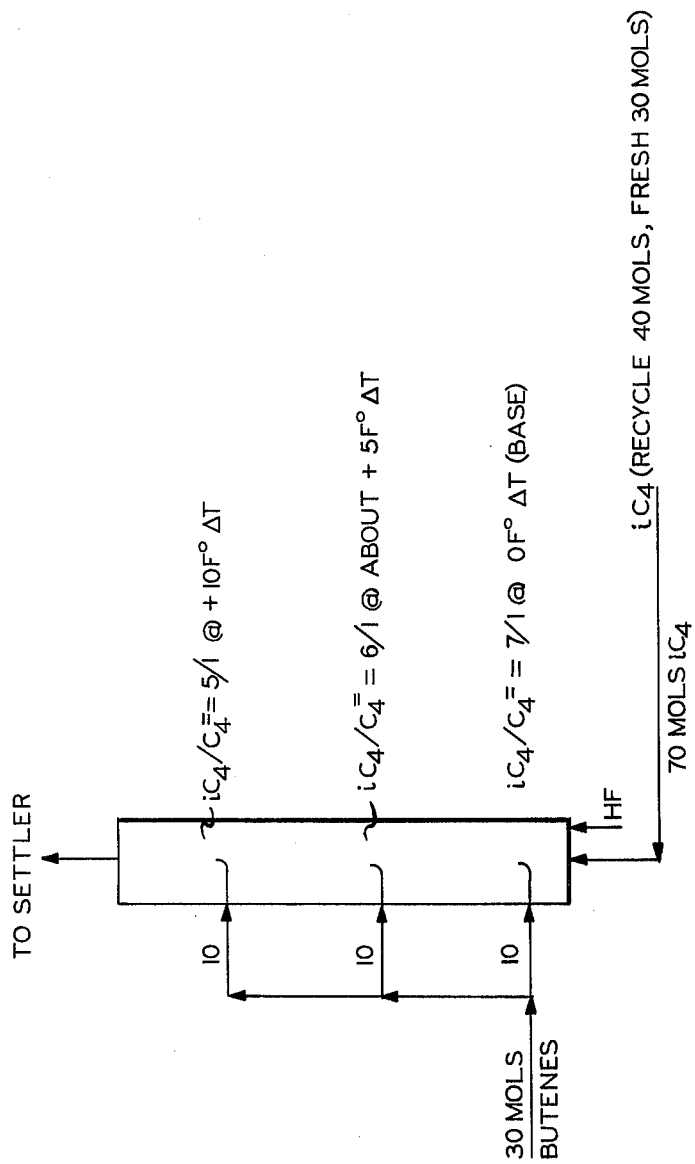
FIGS. 2 and 3 illustrate a conventional operation and operation according to the invention, respectively.
Figure 3:
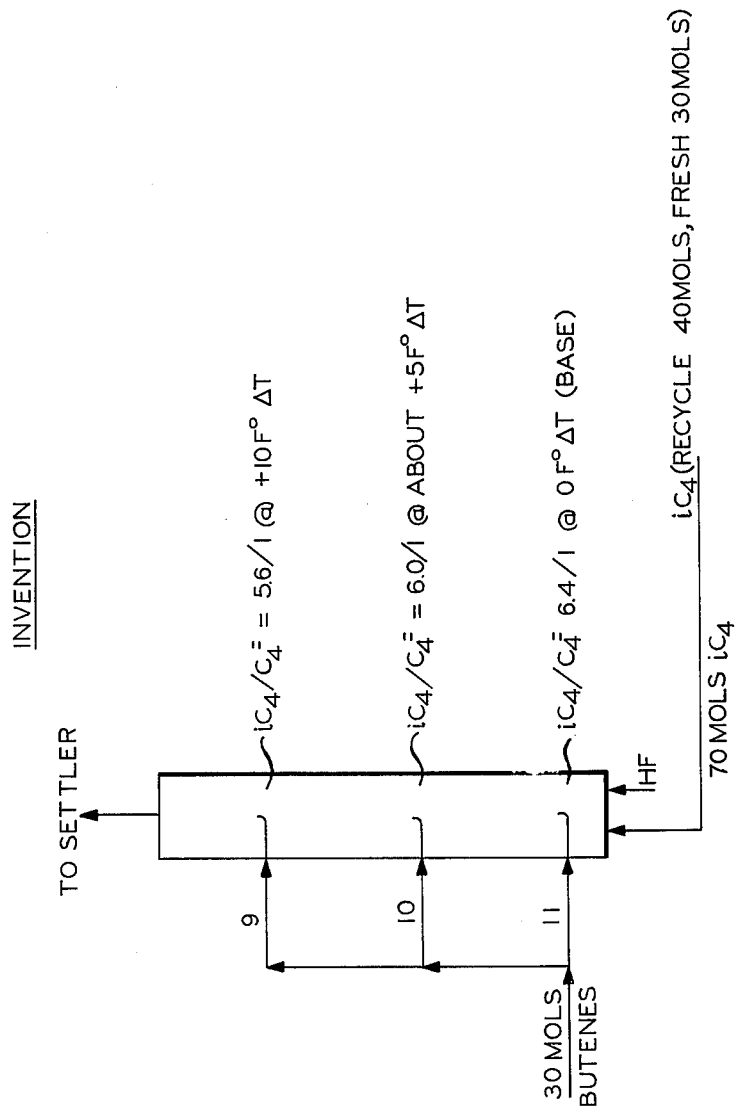

The following calculated example illustrates the advantages of the invention illustrated in FIG. 3 over a conventional operation as illustrated in FIG. 2. Referring to FIGS. 2 and 3, it will be noted that the amount of olefin introduced into the conventional and into the invention operations are the same, the principal difference being that the different amounts of olefin according to the invention are added in decreasing quantities along the flow path to effect higher isobutane-olefin ratios along the flow path to account for detrimental effects of increasing temperature along this flow path.

Calculated ASTM Octanes Relating Isobutane/Olefin Increase with Temperature Increase along Reaction Zone
From page 120, Phillips Petroleum Company's HF Acid Alkylation:

| Reactor | $\Delta T, F°$ | ASTM Octane Change at Constant $iC_4$/Olefin |
|---|---|---|
| Top | +10 | −0.5 |
| Middle | + 5 | −0.25 |
| Bottom (base) | 0 | 0 |

Each 10 F° temperature increase decreases ASTM octane by about 0.5 numbers.)
From page 6, Phillips Petroleum Company's HF Acid Akylation:
From graph (at constant temperature)

| $iC_4$/Olefin, mole | ASTM Octane |
|---|---|
| 5/1 | 91.1 |
| 5.6/1 | 91.6 |
| 6/1 | 91.9 |
| 6.4/1 | 92.2 |
| 7/1 | 92.4 |

Conventional:
Equal increments of butenes ($C_4^=$) along the reactor (parallel flow), series isobutane:

| Reactor Locus | $iC_4/C_4^=$ | ASTM Octane Uncorrected | Correct for $\Delta T$ | Corrected ASTM Octane |
|---|---|---|---|---|
| Top | 5/1 | 91.1 | −0.5 | 90.6 |
| Middle | 6/1 | 91.9 | −0.25 | 91.65 |
| Bottom (base) | 7/1 | 92.4 | 0 | 92.4 |
| | | Average | = | 91.55 |

Invention:
Decreasing increments of $C_4^=$ along the reactor diminishing parallel flow), series isobutane:

| Reactor | ASTM Octane | Correct | Corrected ASTM | Weigh- |
|---|---|---|---|---|

Calculated ASTM Octanes Relating Isobutane/Olefin Increase with Temperature Increase along Reaction Zone
From page 120, Phillips Petroleum Company's HF Acid Alkylation:

| Locus | $iC_4/C_4^=$ | Uncorrected | for $\Delta T$ | Octane | | ted |
|---|---|---|---|---|---|---|
| Top | 5.6 | 91.6 | −0.5 | 91.1 | $\frac{(9)}{(30)}$ | 27.33 |
| Middle | 6.0 | 91.9 | −0.25 | 91.65 | $\frac{(10)}{30}$ | 30.55 |
| Bottom (base) | 6.4 | 92.2 | 0 | 92.2 | $\frac{(11)}{30}$ | 33.81 |
| | | | | Average | = | 91.69 |

The above illustrates that higher octane can be realized by decreasing the size of the butylene incremental injection along the flow, utilizing the same total olefin and same total isobutane.

In addition, the system of the invention produces a more uniform octane product throughout. The prior way has 92.4 − 90.6 or 1.8 Δ octane, while the invention has 92.2 − 91.1 or 1.1 Δ octane numbers, as illustrated.

I claim:

1. In a process for producing alkylate by reacting an olefin with an isoparaffin in the presence of liquid HF acid catalyst, wherein said acid catalyst passes through a cyclic path through a vertical extended reaction zone into a settling zone for separating reaction mass into an alkylate phase and an HF acid phase, and a cooling zone for cooling HF acid phase returning from the settling zone to the inlet end portion of said reaction zone, the steps of producing high octane number alkylate which comprise:
   (a) charging the total isoparaffin feed, including recycle isoparaffin, along with HF acid catalyst to said inlet end portion of said reaction zone forming an upwardly flowing mass that is flowing continuously through said reaction zone,
   (b) introducing separate spaced streams of olefin into said reaction zone in decreasing quantities along the length of the reaction zone, the amounts of olefin introduced at each spaced point being sufficient to effect high isoparaffin to olefin molar ratios along the flow path of said mass, thereby avoiding the detrimental effects of unavoidable increases in reaction temperature along the reaction flow path of said mass, and
   (c) recovering high octane alkylate product from said alkylate phase 2. A process according to claim 1 wherein the isoparaffin is isobutane and the olefin is a mixture of butylenes.

3. a process according to claim 1 wherein the alkylation temperature is in the range of −40° F (−40° C) to about 150° F (66° C), the pressure is sufficient to maintain liquid phase conditions, and the mole ratio of isoparaffin to olefin is in the range of 4:1 to 20:1.

4. A process according to claim 1 wherein the molar ratio of isoparaffin to olefin increases at the point of reaction along the length of the reaction zone with the lowest molar ratio at the inlet end and the highest molar ratio near the outlet end, with the further proviso that the isoparaffin is isobutane and the olefin is a mixture of butylenes.

* * * * *